US006557575B1

(12) United States Patent
Gerhardt et al.

(10) Patent No.: US 6,557,575 B1
(45) Date of Patent: May 6, 2003

(54) FLUID FLOW CONTROL FREEZE/THAW VALVE FOR NARROW BORE CAPILLARIES OR MICROFLUIDIC DEVICES

(75) Inventors: Geoff C. Gerhardt, Milbury, MA (US); Edouard S. P. Bouvier, Stow, MA (US); Theodore Dourdeville, Marion, MA (US)

(73) Assignee: Waters Investments Limited, New Castle, DE (US)

( * ) Notice: Subject to any disclaimer, the term of this patent is extended or adjusted under 35 U.S.C. 154(b) by 0 days.

(21) Appl. No.: 09/997,491

(22) Filed: Nov. 19, 2001

(51) Int. Cl.[7] ............................. F16K 49/00; F17D 1/18
(52) U.S. Cl. ................... 137/13; 137/251.1; 137/828
(58) Field of Search ................. 137/827, 828, 137/251.1, 341, 13

(56) References Cited

U.S. PATENT DOCUMENTS

| 3,663,203 A | | 5/1972 | Davis et al. ............... 75/43 |
|---|---|---|---|
| 4,203,472 A | * | 5/1980 | Dulaney ................. 137/828 |
| 4,258,740 A | | 3/1981 | Kaartinen et al. .......... 137/74 |
| 4,269,212 A | | 5/1981 | Kaartinen ................ 137/13 |
| 4,612,959 A | | 9/1986 | Costello ................ 137/828 |
| 4,766,922 A | | 8/1988 | Kaartinen et al. .......... 137/13 |
| 4,949,742 A | * | 8/1990 | Rando et al. ............. 137/13 |
| 4,989,626 A | | 2/1991 | Takagi et al. ............ 137/13 |
| 5,014,738 A | | 5/1991 | Jones .................. 137/340 |
| 5,101,848 A | | 4/1992 | Kojima et al. ............ 137/13 |
| 5,311,896 A | * | 5/1994 | Kaartinen ................ 137/15 |
| 5,316,262 A | * | 5/1994 | Koebler ................. 251/8 |
| 5,563,352 A | | 10/1996 | Helmig ................ 73/863.12 |
| 5,795,788 A | | 8/1998 | Bevan et al. ............ 436/161 |
| 5,988,197 A | | 11/1999 | Colin et al. ............. 137/13 |
| 6,007,302 A | | 12/1999 | Welle .................. 417/52 |
| 6,041,811 A | | 3/2000 | Walter et al. ............ 137/334 |
| 6,159,744 A | * | 12/2000 | Bevan et al. ............ 436/180 |
| 6,311,713 B1 | * | 11/2001 | Kaartinen ............... 137/13 |

FOREIGN PATENT DOCUMENTS

| FR | 2 422 884 | 11/1979 | ............ F16K/9/00 |
|---|---|---|---|
| WO | WO 86/06144 | 10/1986 | ........... F16K/13/10 |
| WO | WO 94/29690 | 12/1994 | ............ G01N/1/00 |

OTHER PUBLICATIONS

Bevan, et al., "Freeze–Thaw Flow Management: A Novel Concept For High–Performance Liquid chromatography, Capillary Electrophoresis, Electrochromatography And Associated Techniques", *Journal of Chromatography*, 697 (1995) 541–548.

Zhang, et al., "Automated And Integrated System For High–Throughput DNA Genotyping Directly From Blood", *Analytical Chemistry*, 71 (1999) 1138–1145.

Bevan, "A Lab In Lilliput: A Dream Or Reality?", *Cast*, Feb./Mar. 2001, pp.: 10–14.

* cited by examiner

*Primary Examiner*—A. Michael Chambers
(74) *Attorney, Agent, or Firm*—Brian Michaelis; John C. Serio

(57) ABSTRACT

Methods and devices for the management of fluid flow within nanoscale analytical systems, comprising a freeze thaw valve having differing geometries to constrict a frozen plug within the freeze thaw segment. The freeze thaw valve is directed to use in high-pressure analytical systems. The geometry of an inner diameter of a channel or tube within a freeze thaw segment is configured to cause constriction of a freeze plug when axial force is applied. The constriction is used in the flow-path of a freeze thaw valve to prevent movement of the frozen plug at high pressures to avoid valve leakage.

16 Claims, 3 Drawing Sheets

FLUID FLOW CONTROL FREEZE/THAW VALVE FOR NARROW BORE CAPILLARIES OR MICROFLUIDIC DEVICES

FIELD OF THE INVENTION

This invention relates generally to a method and apparatus for controlling liquid flow through nanoscale capillary tubing and channels, by freezing the liquid or thawing the frozen liquid in a segment of the tube or channel.

BACKGROUND OF THE INVENTION

The management of the flow of liquids within small diameter channels presents challenges as the scale of the channels and volumes of the liquids are reduced. One significant constraint is the configuration of traditional valve technology. Nanoliter volume-scale fluid management is severely negatively affected by poorly-swept or "dead" volume that is inherent within traditional valving methods. The method of using a fluid within these nanoscale capillaries and channels to act as its own on/off valve by freezing and thawing that liquid is known in the art, see for example U.S. Pat. Nos. 6,159,744 and 5,795,788. It has been found that the flow of liquids can be diverted to a further channel or chamber by merely freezing and thawing the liquid contained within a segment of tubing or channel. This flow-switching device, that is commonly referred to as "freeze thaw valving", requires no moving parts and most importantly contributes substantially no dead volume within the analytical system.

Prior art freeze thaw valves rely on the resistance to shearing motion that is obtained between a resulting frozen plug and the channel wall to restrict fluid flow during the valve closed state. While this method of fluid management has been successful in analytical systems involving low pressure, experience with these valves at high pressures (e.g. greater than 20,000 p.s.i) reveals that the frozen plug can be displaced from the valving segment resulting in low-level flow or leakage. As the frozen plug is extruded out of the valving segment, new fluid entering the valving segment is solidified maintaining an incomplete valve closure. Unfortunately, this low-level leakage is unacceptable when these freeze thaw valves are used for capillary chromatography and other nanoscale analytical systems where fluid flow rates as low as a few nanoliters per minute and high delivery pressures are used.

SUMMARY OF THE INVENTION

The invention provides methods and devices for the management of fluid flow within high pressure nanoscale analytical systems. The device comprises freeze thaw valves implemented by fluid conduits having differing geometries to restrain the motion of frozen plugs. The freeze thaw valve contemplated by the invention is directed to use in high-pressure analytical systems. The geometry of a fluid conduit within a freeze thaw segment of the valve is configured to cause constriction of at least a portion of a freeze plug, when a hydraulic load is applied to the upstream side of the plug. This geometry is used in the flow path of the freeze thaw valve segment to prevent movement of the frozen plug at high pressures to substantially avoid leakage. The configuration of the freeze thaw segment can be a variety of geometries that cause the constriction of the freeze plug when a hydraulic load is applied.

The fluid conduits contemplated within the invention have transverse dimensions (normal to the flow axis) on the order of approximately 2 $\mu$m to 500 $\mu$m, and more typically 25–100 $\mu$m. The pressures within the analytical systems utilizing the freeze thaw segments contemplated within the invention are on the order of approximately 20,000 PSIG or greater.

Means for freezing the liquid phase within the freeze thaw segment, in an illustrative embodiment, is a finely directed jet of cooling gas. The cooling gas can be provided from a liquefied source of gas under pressure, such as liquid carbon dioxide. Alternative means for freezing the liquid phase, within the freeze thaw segment, include the use of a cryogenic liquid such as liquid nitrogen, or a thermoelectric method such as a Peltier-based heat pump. It is contemplated within the invention, that a warming means for thawing the frozen plug, within the freeze thaw segment, can be a directed jet of warm air or other gas, an electrical resistance heating element, or the ambient air within the analytical environment. The temperature of the freeze thaw segment may be monitored by conventional means known to those skilled in the art such as a thermocouple incorporated into the freeze thaw segment. Further, the cooling means may be applied continuously during the time required to maintain the limiting frozen plug and interrupted by alternative heating means when fluid flow is desired.

Advantages of the invention include provision of a simple and low cost mechanism for implementing freeze thaw valving in high pressure contexts. Migration of the frozen plug and leakage are substantially avoided. The present invention provides methods and apparatus for the management of fluid flow within a nanoscale high pressure analytical system while avoiding introduction of poorly-swept or dead volumes.

BRIEF DESCRIPTION OF DRAWINGS

These and other features and advantages of the present invention will become apparent from the following detailed description taken in conjunction with the accompanying drawings which illustrate the exemplary embodiments of the method and apparatus for freeze thaw valving of the present invention.

DETAILED DESCRIPTION

Figure 1A:
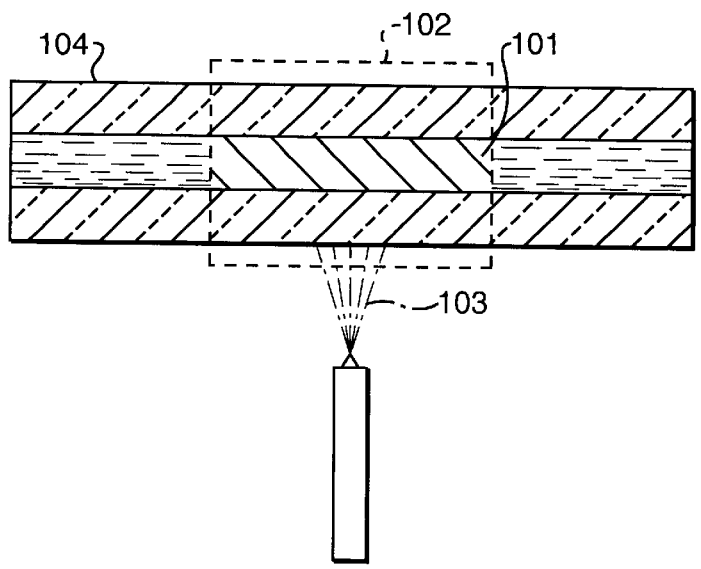
FIGS. 1A, 1B, and 1C depict prior art freeze thaw valving.
Figure 1B:
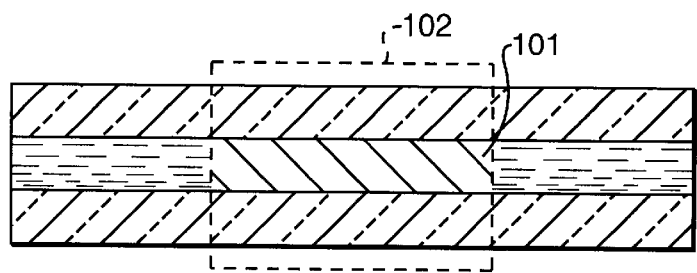
Figure 1C:
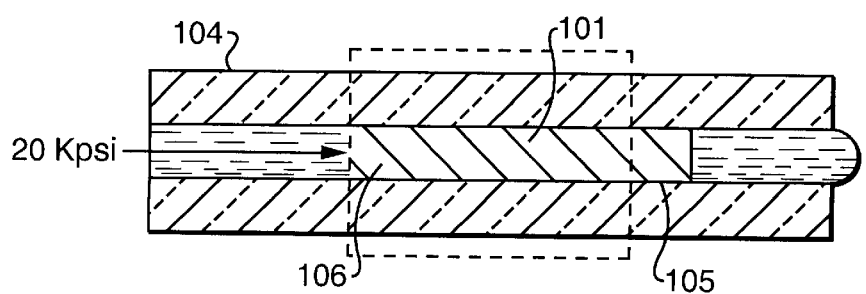

In typical freeze thaw valves a resistance to shearing motion exists between the frozen liquid plug and capillary walls; that resistance is sufficient to restrict fluid flow. However, this method of valving has been found to be problematic as pressures are increased, such as within a high pressure analytical system. Referring to FIGS. 1A and 1B, a typical freeze thaw valve is depicted. In the typical freeze thaw valve a solid plug 101 is formed within a segment of capillary tubing 104 by directing a refrigerant 103 such as carbon dioxide to a selected segment 102 of capillary tubing 104 or channel. As shown in FIG. 1B, the frozen plug 101 is formed causing fluid flow within the selected segment 102 to cease. Turning to FIG. 1C, a high pressure analytical system (e.g. 20,000 p.s.i or greater) is depicted. Within this high pressure analytical system, fluid pressure within the capillary tubing 104 or channel produces an axial force on the frozen plug, which creates a shear stress at the interface between the formed frozen plug 101 and capillary wall 105. A sufficiently high applied fluid pressure will cause the frozen plug 101 to move. The movement of the frozen plug 101 results in valve leakage. While a subsequent frozen plug 106 is formed, the movement of the original frozen plug 101 can be problematic for the downstream analysis.

Figure 2A:
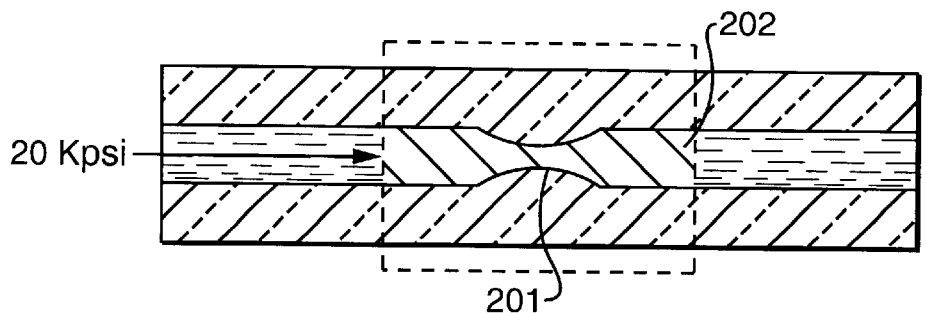
FIGS. 2A and 2B depict configurations used to constrict a freeze plug.

Turning to FIG. 2A, the interior geometry of a capillary tubing is changed to provide a freeze thaw valve that not only relies on the resistance to shearing motion obtained between a frozen plug 202 and the corresponding capillary walls, but also uses a region of convergent geometry within the fluid channel to prevent the frozen plug from moving and causing leakage. A taper 201 is formed within the interior of the capillary to allow constriction of the frozen plug 202 in the presence of an applied hydraulic load, preventing failure and migration of the freeze thaw plug in analytical systems that involve fluid pressures in excess of 20,000 p.s.i. The altered geometry of the freeze thaw segment is formed by tapering the internal dimensions of the capillary tubing or channel to form a convergent region. For example, the capillary internal diameter can be tapered inwardly approximately one-half the normal capillary interior diameter over a length of approximately one times the normal capillary interior diameter (e.g. for a 100 $\mu$m capillary a taper to 50 $\mu$m over a length of 100 $\mu$m) in order to facilitate the constriction feature or mechanism.

Figure 2B:
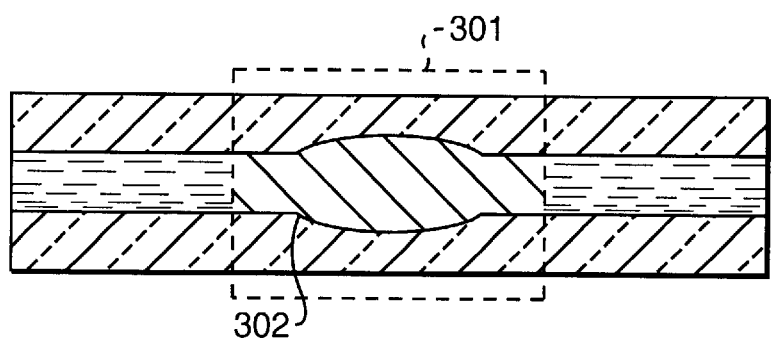

As shown in FIG. 2B, an illustrative alternative embodiment has a freeze thaw segment 301 having an interior channel 302 with a geometry that is bulbous in configuration, including a divergent region followed by a convergent region. As in the above inventive freeze thaw valves, the geometry of this embodiment imparts, in addition to the resistance to shearing motion utilized in prior art valves, constriction forces that allow its use in high pressure analytical systems. In this embodiment the capillary interior diameter is increased to approximately one and one-half times the normal capillary interior diameter over a length of three times the normal capillary interior diameter to form the constriction mechanism.

Figure 3:
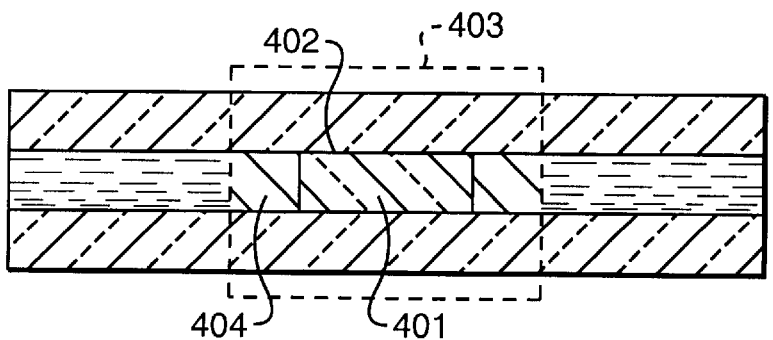
FIG. 3 depicts a porous frit bonded to a capillary wall to constrict a freeze plug.

Turning to FIG. 3, a further illustrative alternative embodiment is shown. In this alternative embodiment, a porous frit 401 is bonded to a capillary wall 402 forming a freeze thaw valve segment 403. As in the above inventive freeze thaw valves, the configuration of this embodiment provides a frozen plug 404 within the freeze thaw segment with not only a resistance to shearing motion between the plug and the capillary wall, but also constriction forces that allow the use of this embodiment in high pressure analytical systems. In this illustrative embodiment the frit 401 is formed by polymerizing sodium silicate in situ over a length of approximately two times the capillary interior diameter. The frit 401 prepared in this way forms covalent linkages to the capillary wall thereby maintaining a stationary position. The frit 401 has a pore size of approximately 0.5 $\mu$m. Within this porous frit 401, the fluid pathways or interstitial spaces include repeated instances where convergent geometry is obtained.

Figure 4:
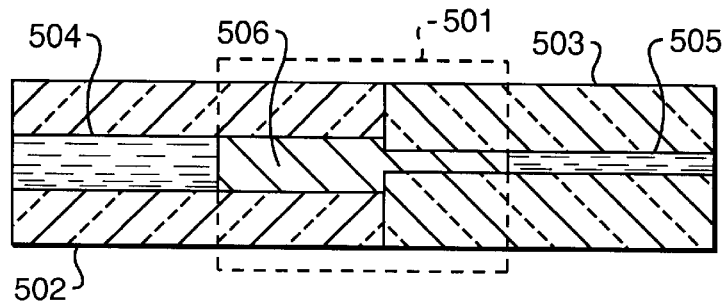
FIG. 4 depicts capillaries having different diameter to constrict a freeze plug.

As shown in FIG. 4, an additional illustrative alternative embodiment has a freeze thaw segment 501 that has a proximal capillary 502 having a first interior diameter 504 and a distal capillary 503 having a second interior diameter 505. The proximal capillary 502 is joined with the distal capillary 503 forming the freeze thaw segment 501. The first interior diameter 504 is larger than the second interior diameter 505. The difference in the diameter of the first interior and the second interior diameters imparts to the freeze thaw segment 501 a configuration that allows a frozen plug 506 to be held in place by not only the resistance to shearing motion obtained at the interface between the plug and the capillary wall, but constrictive forces that are caused by the differing diameters.

Figure 5:
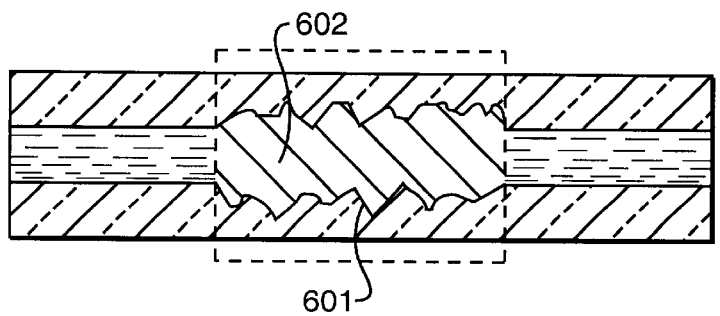
FIG. 5 depicts chemical modification of capillary walls to impart surface roughness.

As illustrated in FIG. 5, a further alternative embodiment provides a freeze thaw segment having changes to its interior capillary walls 601. Chemical modifications of the interior capillary wall, by methods known to those skilled in the art, such as filling a capillary with 1N NaOH for approximately 24 hours at 25° C., produces a capillary wall that is rough in texture. This rough surface allows a frozen plug 602 to be held in place by not only resistance to shearing motion obtained at the interface between the plug and the capillary wall, but also constrictive forces that are created where regions of divergent geometry are followed by regions of convergent geometry.

Figure 6:
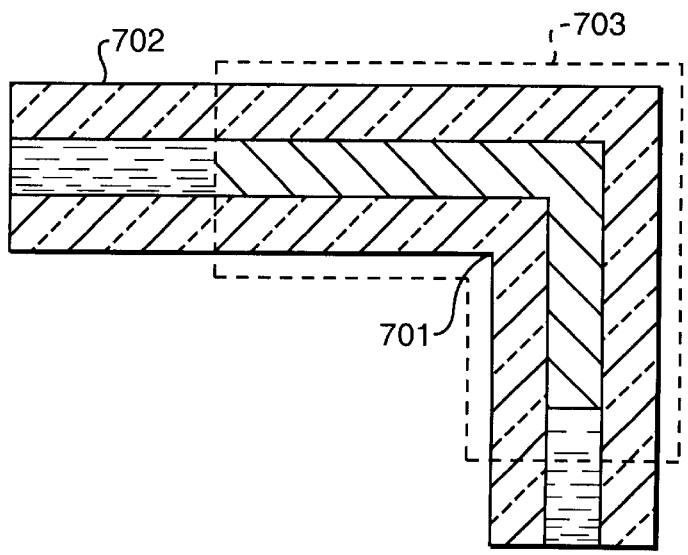
FIG. 6 depicts a bend in a capillary tube used to constrict a freeze plug.

In FIG. 6, yet a further alternative embodiment having a freeze thaw segment 703 containing a bend 701 in a capillary tubing 702 or channel. This bend 701, within the freeze thaw segment 703, imparts constrictive forces that allow a frozen plug to be held in place by not only resistance to shearing motion obtained between the plug and the capillary wall, but also constrictive forces that are caused by the non-linear shape of the freeze thaw segment 703.

The freeze thaw valves according to the invention can be manufactured by methods known to those skilled in the art. Capillary or channel composition will be a function of structural requirements, manufacturing processes, and reagent compatibility/chemical resistance properties. The choice of materials will depend on a number of factors such as ease in manufacturing and inertness to fluids that will flow through the nanoscale channels or capillary tubing, as is known to those skilled in the art. Specifically, capillary tubing and channels are provided that are made from inorganic crystalline or amorphous materials, e.g. silicon, silica, quartz, inert metals, or from organic materials such as plastics, for example, poly(methyl methacrylate) (PMMA), acetonitrile-butadiene-styrene (ABS), polycarbonate, polyethylene, polystyrene, polyolefins, polypropylene, polyphenylene sulphide (PPS), PEEK, and metallocene. Capillary tubing and channels according to the invention can be fabricated from thermoplastics such as polyethylene, polypropylene, methylmethacrylates, polycarbonates, and certain Teflons, among others, due to their ease of molding, stamping and milling. Alternatively, capillary tubing and channels can be made of silica, glass, quartz or inert metal.

Although the present disclosure is described in detail with respect to chromatographic applications and specifically capillary chromatography where flow rates as low as 5 nanoliters per minute are used, it is contemplated that embodiments of the present invention can also be directed to industrial and process control applications as well.

Although the inventive freeze thaw valve is discussed in terms of nanoscale applications, it should be appreciated that the configurations disclosed herein can be adapted to much larger scale channels or tubes where liquids under high pressure are used. Although specific geometries have been set forth in the above illustrative embodiments, it should be appreciated that the configurations disclosed herein are not an exhaustive illustration of geometries or configurations that can be used. It should be further appreciated that any of various configuration that impart compressive or constrictive forces to a freeze plug within a freeze thaw segment, in the presence of an applied hydraulic load, can be utilized.

Various other changes, omissions and additions in the form and detail of the present invention may be made therein without departing from the spirit and scope of the invention. Therefore, the above description should not be construed as limiting, but merely as exemplification of the various embodiments.

What is claimed is:

1. A method for managing liquid flow through tubing or channels by freezing and thawing the liquid within a segment of capillary tubing or channels comprising the steps of:

configuring a valve segment of an interior passage of said tubing or channels to have a geometry that resists shear forces upon a frozen plug within said interior diameter without decreasing the volume of said valve segment;

freezing the valve segment to stop the passage of fluids; and thawing the valve segment to allow the passage of fluids.

2. The method of claim 1 wherein said interior passage is contained within a capillary tubing.

3. The method of claim 1 wherein said interior passage is a micro-channel.

4. The method of claim 1 wherein said liquid flow is under high pressure greater than 20,000 p.s.i.

5. The method of claim 1 wherein said freezing of said valve segment is by the use of carbon dioxide.

6. The method of claim 1 wherein said freezing of said valve segment is by the use of a heat pump.

7. The method of claim 1 wherein said geometry is bulbous.

8. The method of claim 1 wherein said geometry has a first substantially uniform diameter and a second substantially uniform diameter and said first substantially uniform diameter is greater than said second substantially uniform diameter and the second substantially uniform diameter is the diameter of said tubing or channel.

9. The method of claim 1 wherein said geometry is a bend and said interior diameter of said valve segment is substantially uniform.

10. An apparatus for managing liquid flow through tubing or channels by freezing and thawing the liquid within a segment of capillary tubing or channel comprising:

a valve segment having an interior diameter for fluid flow;

a geometry within said interior diameter wherein said geometry does not decrease the volume of said interior diameter of said valve segment;

a means for freezing said fluid within said valve segment forming a frozen plug; wherein said frozen plug stops fluid flow and is held in place by forces created by said geometry; and a means for thawing said fluid within said valve segment to allow fluid flow.

11. The apparatus of claim 10 wherein said liquid flow is under high pressure greater than 20,000 p.s.i.

12. The apparatus of claim 10 wherein said means for freezing said valve segment is by the use of carbon dioxide.

13. The apparatus of claim 10 wherein said means for freezing said valve segment is by the use of a heat pump.

14. The apparatus of claim 10 wherein said geometry is bulbous.

15. The apparatus of claim 10 wherein said geometry has a first substantially uniform diameter and a second substantially uniform diameter and said first substantially uniform diameter is greater than said second substantially uniform diameter and said second substantially uniform diameter is the same diameter of said tubing or channel.

16. The apparatus of claim 10 wherein said geometry is a bend and said interior diameter of said valve segment is substantially uniform.

* * * * *